(12) United States Patent
Menander et al.

(10) Patent No.: US 6,177,471 B1
(45) Date of Patent: *Jan. 23, 2001

(54) METHOD FOR TREATING PATIENTS WITH ACNE BY ADMINISTERING A CGMP-SPECIFIC PDE INHIBITOR

(75) Inventors: Kerstin B. Menander, Meadowbrook; Mark Jeffrey Mayle, Warrington, both of PA (US)

(73) Assignee: Cell Pathways, Inc., Horsham, PA (US)

(*) Notice: Under 35 U.S.C. 154(b), the term of this patent shall be extended for 0 days.

This patent is subject to a terminal disclaimer.

(21) Appl. No.: 09/378,660

(22) Filed: Aug. 20, 1999

Related U.S. Application Data

(63) Continuation-in-part of application No. 09/239,840, filed on Jan. 29, 1999, now Pat. No. 6,025,394.

(51) Int. Cl.⁷ ................................................. A61K 31/19
(52) U.S. Cl. ............................................................ 514/569
(58) Field of Search ............................................. 514/569

(56) References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,865,840 | 2/1975 | Carson . |
| 3,920,636 | 11/1975 | Takahashi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,076,711 | 2/1978 | Ganguly et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,393,063 | 7/1983 | Moncada . |
| 4,423,075 | 12/1983 | Dvornik et al. . |
| 4,457,927 | 7/1984 | Biere et al. . |

(List continued on next page.)

FOREIGN PATENT DOCUMENTS

| | | |
|---|---|---|
| 3038166 | 5/1981 | (DE) . |
| 274218 | 12/1989 | (DE) . |
| 0 330004 A1 | 8/1989 | (EP) . |
| 0 347 146 A2 | 12/1989 | (EP) . |
| 0 349239 A2 | 1/1990 | (EP) . |
| 0 351058 A1 | 1/1990 | (EP) . |
| 0 352960 A2 | 1/1990 | (EP) . |
| 0 395328 A2 | 10/1990 | (EP) . |
| 0 428268 A2 | 5/1991 | (EP) . |
| 0 463756 A1 | 1/1992 | (EP) . |
| 0 485157 A2 | 5/1992 | (EP) . |
| 0 485158 A2 | 5/1992 | (EP) . |
| 0 485171 A2 | 5/1992 | (EP) . |
| 0 485172 A2 | 5/1992 | (EP) . |
| 0 485173 A2 | 5/1992 | (EP) . |
| 0 508586 A1 | 10/1992 | (EP) . |
| 0 526004 A1 | 2/1993 | (EP) . |
| 0 607439 A1 | 7/1994 | (EP) . |
| 0 722 937 A1 | 7/1996 | (EP) . |
| 0 743304 A1 | 11/1996 | (EP) . |

(List continued on next page.)

OTHER PUBLICATIONS

Royer E., et al., Cyclic AMP and Cyclic GMP Production in Normal and Psoriatic Epidermis, *Dermatoligica*, 165: 533–543 (1982).

Waddell, W.R. et al., Sulindac for Polyposis of the Colon, Am. J. Surgery, vol. 157, pp. 175–179 (1989).

Gonzaga, R.A.F. et al., Sulindac Treatment for Familial Polyposis Coli, The Lancet, p. 751, Mar. 30, 1985.

Waddell, W.R. et al., Sulindac for Polyposis of the Colon, J. Surg. Oncology, vol. 24, pp. 83–87 (1983).

Van Arman, C.G. et al., Pharmacologic Properties of an Antiinflammatory Agent, 5–fluoro–2–methyl–1–(p–methylsulfinyl benzylidene)–inden–3–yl–acetic acid, Federation Proceedings (1972) of the Federation of American Societies for Experimental Biology abstract No. 2044.

Hucker, H.B. et al., Metabolism of a New Antiinflammatory Agent, cis–5–fluoro–2–methyl–1–(p–methylsulfinyl)–benzylidene–inden–3–acetic acid In Men and Animals, Federation Proceedings (1972) of the Federation of American Societies for Experimental Biology abstract No. 2045.

Gilman, S.C. et al., Nonsteroidal Anti–Inflammatory Drugs in Cancer Therapy, (circa 1985), pp. 157–179.

Brogden, R.N. et al., Sulindac: A Review of its Pharmacological Properties and Therapeutic Efficacy in Rheumatic Diseases, Drugs, vol. 16, pp. 97–114 (1978).

Hucker, H.B. et al., Hysiologic Disposition and Metabolic Fate of a New Anti–Inflammatory Agent, cis–5–fluoro–2–methyl–1–[p–(methylsulfinyl)–benzylidenyl]–indene–3–acetic acid in the Rat, Dog, Rhesus Monkey, and Man, Drug Metabolism and Disposition, vol. 1, No. 6, pp. 721–736 (1973).

(List continued on next page.)

Primary Examiner—Raymond Henley, III
(74) Attorney, Agent, or Firm—Brinks Hofer Gilson & Lione

(57) ABSTRACT

Inhibitors of cGMP-specific PDE are useful in the treatment of acne.

1 Claim, No Drawings

U.S. PATENT DOCUMENTS

| | | |
|---|---|---|
| 4,460,590 | 7/1984 | Möller . |
| 4,460,591 | 7/1984 | DeGraw et al. . |
| 4,751,224 | 6/1988 | Agarwal et al. . |
| 4,880,810 | 11/1989 | Lowe, III et al. . |
| 4,885,301 | 12/1989 | Coates . |
| 4,923,874 | 5/1990 | McMahon et al. . |
| 4,971,972 | 11/1990 | Doll et al. . |
| 5,011,843 | 4/1991 | Shell . |
| 5,073,559 | 12/1991 | Coates . |
| 5,091,431 | 2/1992 | Tulshian et al. . |
| 5,147,875 | 9/1992 | Coates et al. . |
| 5,175,151 | 12/1992 | Afonso et al. . |
| 5,223,501 | 6/1993 | Chakravarty et al. . |
| 5,239,083 | 8/1993 | Kumazawa et al. . |
| 5,250,535 | 10/1993 | Verheyden et al. . |
| 5,254,571 | 10/1993 | Coates et al. . |
| 5,358,952 | 10/1994 | Moschel et al. . |
| 5,376,683 | 12/1994 | Klar et al. . |
| 5,393,755 | 2/1995 | Neustadt et al. . |
| 5,401,754 | 3/1995 | Fujioka et al. . |
| 5,401,774 | 3/1995 | Pamukcu et al. . |
| 5,439,895 | 8/1995 | Lee et al. . |
| 5,464,861 | 11/1995 | Dobrusin et al. . |
| 5,488,055 | 1/1996 | Kumar et al. . |
| 5,500,230 | 3/1996 | Nathanson . |
| 5,614,530 | 3/1997 | Kumar et al. . |
| 5,614,627 | 3/1997 | Takase et al. . |
| 5,674,876 | 10/1997 | Gilbert et al. . |
| 5,696,159 | 12/1997 | Gross et al. . |
| 5,728,563 | 3/1998 | Tanaka . |
| 5,756,818 | 5/1998 | Buchmann et al. . |
| 5,852,035 | 12/1998 | Pamukcu et al. . |
| 5,858,694 | 1/1999 | Piazza et al. . |
| 5,869,519 | 2/1999 | Karanewsky et al. . |
| 5,874,035 | 2/1999 | Pamukcu et al. . |
| 6,025,394 * | 2/2000 | Menander et al. .................. 514/569 |

FOREIGN PATENT DOCUMENTS

| | | |
|---|---|---|
| 807826 | 1/1959 | (GB) . |
| 2063249 | 6/1981 | (GB) . |
| 56-53658 | 5/1981 | (JP) . |
| 57-167974 | 10/1982 | (JP) . |
| 59-229468 | 5/1986 | (JP) . |
| 8-311035 | 11/1996 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| WO 94/19351 | 9/1994 | (WO) . |
| WO 94/29277 | 12/1994 | (WO) . |
| WO 95/18969 | 7/1995 | (WO) . |
| WO 95/26743 | 10/1995 | (WO) . |
| WO 96/32379 | 10/1996 | (WO) . |
| WO 97/03070 | 1/1997 | (WO) . |
| WO 97/03985 | 2/1997 | (WO) . |
| WO 97/24334 | 7/1997 | (WO) . |
| WO 98/08848 | 3/1998 | (WO) . |
| WO 98/14448 | 4/1998 | (WO) . |
| WO 98/15530 | 4/1998 | (WO) . |
| WO 98/16521 | 4/1998 | (WO) . |
| WO 98/17668 | 4/1998 | (WO) . |
| WO 98/19224 | 4/1998 | (WO) . |
| WO 98/23597 | 6/1998 | (WO) . |
| WO 98/38168 | 9/1998 | (WO) . |

OTHER PUBLICATIONS

Shen, T.Y. et al., Chemical and Biological Studies on Indomethacin, Sulindac and Their Analogs, pp. 170–178 (circa 1975).

Duggan, D.E. et al., The disposition of sulindac, Clin. Pharm. and Therapeutics, vol. 21, No. 3, pp. 326–335 (1976).

Duggan, D.E. et al., Identification of the Biologically Active Form of Sulindac, J. Pharm. and Exper. Therap., vol. 201, No. 1, pp. 8–13 (1977).

Glavin, G.B. et al., The Effects of Sulindac and its Metabolites on Acute Stress–Induced Gastric Ulcers in Rats, Toxicology and Applied Pharmacology, vol. 83, pp. 386–389 (1986).

Moorghen, M. et al., A Protective Effect of Sulindac Against Chemically–Induced Primary Colonic Tumours in Mice, Journal of Pathology, vol. 156, pp. 341–347 (1988).

Moorghen, M. et al., The effect of sulindac on colonic tumour formation in dimethylhydrazine–treated mice, Acta Histochemica, Suppl.–Band XXXIX, S. pp. 195–199 (1990).

Bjarnason et al., Clinicopathological Features of Nonsteroidal Antiinflammatory Drug–Induced Small Intestinal Strictures, Gastroenterology, vol. 94, No. 4, pp. 1070–1074 (1988).

Badrieh, Y., et al., Some Unusual Reactions of 1,2–Bis(phenylethynyl)benzene with Sulfur, Carbon, Monoxide and Alkyl Acetylenedicarboxylates, Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1224–1225, Dec. 4, 1976.

Pepin, P. et al., Effects of Sulindac and Oltipraz on the tumorigenicity of 4–(methylnitrosamino)1–(3–pyridyl)–1–butanone in A/J mouse lung, Carcinogenesis vol. 13, No. 3, pp. 341–348 (1992).

Nicholson, C.D. et al., Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H–S. et al., Effects of Selective Inhibitors on Cyclic Nucleotide Phosphodiesterases of Rabbit Aorta, Biochemical Pharmacology, vol. 38, No. 19, pp. 3331–3339 (1989).

Lugnier, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium nitroprusside, Br. J. Pharmacol., vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, pp. 1198–1204 (1994).

Ferreira, S.H. et al., The molecular mechanism of action of peripheral morphine analgesia: stimulation of the cGMP system via nitric oxide release, European Journal of Pharmacology, vol. 201, pp. 121–122 (1991).

Hidaka, H. et al., Selective Inhibitors of Three Forms of Cyclic Nucleotide Phosphodiesterase—Basic and Potential Clinical Applications, Advances in Cyclic Nucleotide and Protein Phosphorylation Research, vol. 16, pp. 245–259 (1984).

Tulshian, D. et al., Synthesis and Phosphodiesterase Activity of Carboxylic Acid Mimetics of Cyclic Guanosine 3',5'–Monophosphate, J. Med. Chem., vol. 36, pp. 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073–2081 (1992).

Broughton, B.J. et al., Antiallergic Activity of 2–Phenyl–8–azapurin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharmacology, vol. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–97 (1988).

Lichtner, R. B. et al., The Pyrimido–pyrimidine Derivatives RA 233 and RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res., vol. 40, pp. 1950–1954 Jun., 1980.

Bergstrand, H. et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, vol. 13, pp. 38–43 (1977).

Drees, M. et al., 3',5'–Cyclic Nucleotide Phosphodiesterase in Tumor Cells as Potential Target for Tumor Growth Inhibition, Cancer Research, vol. 53, pp. 3058–3061 (1993).

Semmler, J. et al., Xanthine derivatives: comparison between suppression of tumour necrosis factor–α production and inhibition of cAMP phosphodiesterase activity, Immunology, vol. 78, pp. 520–525 (1993).

Mehta, R.G. et al., Structure–Activity Relationships of Brassinin in Preventing the Development of Carcinogen–Induced Mammary Lesions in Organ Culture, Anticancer Research, vol. 14, pp. 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter, S.K. et al., Chemotherapy of Cancer, pp. 362–365, 2d Ed., John Wiley & Sons, NY, NY, (1981).

Biddle, W. et al., Antineoplastic Effect of the Pyrimido–Pyrimidine Derivative: RA 233, Path. Biol., vol. 32, NO. 1, pp. 9–13 (1984).

Clarke, W. R. et al., The type III phosphodiesterase inhibitor milrinone and type V PDE inhibitor dipyridamole individually and synergistically reduce elevated pulmonary vascular resistance (Abstract Only), Pulm. Pharmacol., vol. 7, No. 2, pp. 81–89 (1994).

Raeburn, D. et al., Effects of isoenzyme–selective inhibitors of cyclic nucleotide phosphodiesterase on microvascular leak in guinea pig airways in vivo (Abstract Only), J. Pharmacol. Exp. Ther., vol. 267, No. 3, pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol., vol. 44, No. 5, pp. 1027–1035 (1993).

Barnett, M.S. et al., Initial biochemical and functional characterization of cyclic nucleotide phosphodiesterase isozymes in canine colonic smooth muscle (Abstract Only), J. Pharmacol. Exp. Ther., vol. 264, No. 2, pp. 801–812 (1993).

Molnar–Kimber, K. et al., Modulation of TNFα and IL–1β from endo–toxin–stimulated monocytes by selective PDE isozyme inhibitors (Abstract Only), Agents Actions, vol. 39 (Spec. Conf. Issue), C77–C79 (1993).

Giorgi, M. et al., Characterization of 3':5' cyclic nucleotide phosphodiesterase activities of mouse neuroblastoma N18TG2 cells (Abstract Only), FEBS Lett., vol. 324, No. 1, pp. 76–80 (1993).

Porter, R. et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Apr. 16, 1992).

Molnar–Kimber, K. L. et al., Differential regulation of TNF–α and IL–1β production from endotoxin stimulated human monocytes by phosphodiesterase inhibitors (Abstract Only), Mediators Inflammation, vol. 1, No. 6, pp. 411–417 (1992).

Radomski, M.W. et al., Human colorectal adenocarcinoma cells: differential nitric oxide synthesis determines their ability to aggregate platelets (Abstract Only), Cancer Res., vol. 51, No. 22, pp. 6073–6078 (1991).

Anderson, T.L.G. et al., Interactions between isoprenaline, sodium nitroprusside, and isozyme–selective phosphodiesterase inhibitors on ADP–induced aggrtation and cyclic nucleotide levels in human platelets (Abstract Only), J. Cardiovasc. Pharmacol., vol. 18, No. 2, pp. 237–242 (1991).

Souness, J.E. et al., Role of selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol., vol. 98, No. 3, pp. 725–734 (1989).

Lichtner, R.B. et al., The pyrimidopyrimidine derivatives RA233 and RX–RA85 affect cell cycle distribution of two murine tumor cell lines (Abstract Only), Eur. J. Cancer Clin. Oncol., vol. 25, No. 6, pp. 945–951 (1989).

Mamytbekova, A. et al., Antimetastatic effect of flurbiprofen and other platelet aggregation inhibitors (Abstract Only), Neoplasma, vol. 33, No. 4, pp. 417–421 (1986).

Hagiwara, M. et al., Effect of 1–(3–chloroanilino)–4–phenylpthalazine (MY–5445), a specific inhibitor of cyclic GMP phosphodiesterase, on human platelet aggregation (Abstract Only), J. Pharmacol. Exp. Ther., vol. 228, No. 2, pp. 467–471 (1984).

Ahn, H–S. et al., Potent Tetracyclic Guanine Inhibitors of PDE1 and PDE5 Cyclic Guanosine Monophosphate Phosphodiesterases with Oral Antihypertensive Activity, J. Med. Chem., vol. 40, pp. 2196–2210 (1997).

Mitchell, J.A. et al., Selectivity of nonsteroidal antiinflammatory drugs as inhibitors of constitutive and inducible cyclooxygenase, Proc. Natl. Acad. Sci., vol. 90, pp. 11693–11697, Dec. 1994.

Gaffen, J.D. et al., Increased killing of malignant cells by giving indomethacin with methotrexate, Chemical Abstracts, XP002084860, vol. 106, No. 11, p. 30, col. 1, Mar. 16, 1987.

Tsou, K–C. et al., 5'–Nucleotide Phosphodiesterase Isozyme–V as a Marker for Liver Metastases in Breast Cancer Patients, Cancer, vol. 54, pp. 1788–1793 (1984).

Epstein, P.M. et al., Increased Cyclic Nucleotide Phosphodiesterase Activity Associated with Proliferation and Cancer in Human and Murine Lymphoid Cells (Abstract Only), Cancer Res., vol. 37, No. 11, pp. 4016–4023 (1977).

Sharma, R.K. et al., $Ca^{2+}$/Calmodulin–Dependent Cyclic Nucleotide Phosphodiesterase (PDE1), in Phos. Inh., pp. 65–134, Academic Press. 1996.

Menashi et al., The extracellular matrix produced by bovine corneal endothelial cells contains progelatinase A; FEBS Letters, 361 pp. 61–64 (1995).

Volpert et al., Captopril Inhibits Angiogenesis and Slows the Growth of Experimental Tumors in Rats; J. Clin. Invest., vol. 98, No. 3, pp. 671–679 (Aug. 1996).

Isner, Jeffrey, The Role of Angiogenic Cytokines in Cardiovascular Disease; Clinical Immunology and Immunopathology, vol. 80, No. 3, pp. S82–S91 (Sep. 1996).

Sakamoto et al., Effect of Intravitreal Administration of Indomethacin on Experimental Subretinal Neovascularization in the Subhuman Primate; Arch Ophthalmol, vol. 113, pp. 222–226 (Feb. 1995).

Thölen et al., Die Behandlung der altersabhängigen Makuladegeneration mit Interferon–α–2a; Opthalmologe, vol. 90, pp. 279–282, (1993).

Clements et al., Abstract, Anti–glycated albumin therapy ameliorates early retinal microvascular pathology in db/db mice; J Diabetes Complications, vol. 12(1), pp. 28–33 (Jan. 1998).

Vialettes et al., Perspectives D'Avenir Dans Le Traitement De La Retinopathie Diabetique; Diabete & Metabolisme, vol. 20, pp. 229–234 (1994).

Skopinska–Rozewska et al., Abstract, Inhibition of Angiogenesis by Sulindac and its Sulfone Metabolite (FGN–1): A Potential Mechanism For Their Antineoplastic Properties; Interscience World Conference on Inflammation, Antirheumatics, Analgesics, Immunomodulators; Geneva, Switzerland. May 19–21, 1997.

* cited by examiner

METHOD FOR TREATING PATIENTS WITH ACNE BY ADMINISTERING A CGMP-SPECIFIC PDE INHIBITOR

This application is a continuation in part of U.S. patent application Ser. No. 09/239,840 filed Jan. 29, 1999, now U.S. Pat. No. 6,025,394, which is incorporated herein by reference.

BACKGROUND OF THE INVENTION

Acne is a skin disease that often scars those afflicted, and can afflict patients at young ages—typically teen years—when their self-images are the most sensitive. The scarring is commonly permanent even if the condition is treated with medications. Some patients experience symptoms well into their adult years.

Acne is believed to be caused typically when the sebaceous glands become clogged due to skin cell debris and an excess of a specific type of skin bacteria. Sebaceous glands are located within the dermis layer of the skin along the hair shaft. Keratin and other chemicals associated with the skin can clog the hair shaft and the sebaceous gland. The bacteria, *Propionibacterium acnes* (*P. acnes*), which is always present, multiplies to a much greater degree when the sebaceous glands are clogged because the bacteria prefer an anaerobic environment, which is present when the glands become clogged.

*P. acnes* produces a lipase enzyme that hydrolyzes triglycerides of the sebaceous gland into free fatty acids. The fatty acids along with bacterial proteins and keratin can irritate the skin tissues. This may lead to an inflammatory response and the formation of an acne lesion.

Although the exact cause of acne is unknown, hormones, genetics, and environmental factors all seem to play a role. Androgens, such as testosterone, play an important role in the development of acne lesions. This is evidenced by the correlation between the onset of puberty and the development of acne, and the fact that acne is generally more severe in males than in females.

The type of acne treatments currently recommended depend on the type and the severity of the acne. A few over-the-counter medications (e.g., benzoyl peroxide and salicylic acid) can be used for mild forms of acne, but are ineffective for the moderate and severe cases of acne.

Tretinoin (Retin-A) is often used in combination with or as a replacement for treatment with benzoyl peroxide. Tretinoin is a derivative of vitamin A and is available for topical use. It acts to prevent comedone formation through its anti-keratinization effect. The side effects of tretinoin include heightened sensitivity to exposure to sunlight and local irritation.

Topical antibiotics are sometimes used for treatment of patients with mild to moderate inflammatory acne, but are ineffective against more severe inflammatory acne. To the extent antibiotics have effects against more severe (i.e. inflammatory) forms of acne, the antibiotics must be systemically administered, usually at high doses (e.g., 500 to 2,000 mg/day) initially followed by maintenance doses (e.g., 250–500 mg/day). The most commonly prescribed antibiotic is tetracycline, but erythromycin and minocycline are also used. Such antibiotics, particularly at high doses can lead to side effects including gastrointestinal symptoms such as nausea, vomiting, abdominal pain, diarrhea, rashes, and other allergic reactions. Tetracyclines also can cause fetal harm if used during pregnancy.

Hormone therapy is another approach to treatment of acne based on the involvement of androgens in the development of acne. Estrogen therapy can be effective, but its usefulness is particularly limited in males by side effects such as gynecomastia, suppression of the testes, and uncertain effects on skeletal growth.

Isotretinoin (ACCUTANE) has been used in the treatment of severe nodulocystic acne. ACCUTANE therapy can lead to improvement in acne and can, in some cases exhibit the potential to prevent most permanent scarring from inflammatory acne. The severe side effects of ACCUTANE, however, are often prohibitive. Dry skin, dry eyes, headache, hair thinning, musculoskeltal pain, and other complications may result from treatment with ACCUTANE. Due to its teratogenicity, ACCUTANE should not be used by women who are pregnant or might become pregnant.

Thus, to date, there is typically a trade-off between efficacy and side effects, particularly in the treatment of more severe forms of acne. Accordingly, an effective treatment of acne, particularly its more severe forms, with clinically insignificant side effects is desired.

BRIEF SUMMARY OF THE INVENTION

This invention relates to a method for treating acne by administering to an afflicted patient a therapeutically effective amount of a cGMP-specific phosphodiesterase ("PDE") inhibitor. With such an inhibitor, acne can be treated with minimal side effects associated with conventional acne medications.

DETAILED DESCRIPTION OF THE INVENTION

An example of a cGMP-specific PDE inhibitor is a compound of Formula

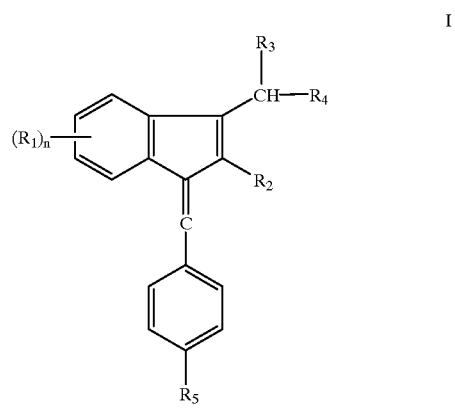

I wherein $R_1$ is independently selected in each instance from the group consisting of hydrogen, halogen, lower alkoxy, hydroxy, lower alkyl, lower alkyl mercapto, lower alkylsulfonyl, lower alkylamino, di-lower alkyl amino, amino, nitro, nitrile, lower alkyl carboxyl ate, —$CO_2H$, and sulfonamido;

$R_2$ is selected from the group consisting of hydrogen and lower alkyl;

$R_3$ is selected from the group consisting of hydrogen, lower alkyl, hydroxy, and amino;

$R_4$ is selected from the group consisting of -COM and $CH_2OH$ wherein M is selected from the group consisting of hydroxy, substituted lower alkoxy, amino, alkylamino, dialkylamino, N-morpholino, hydroxyalkylamino, polyhydroxyamino, dialkylaminoalkylamino, aminoalklyamino, and the group OMe, wherein Me is a cation;

$R_5$ is an alkyl sulfonyl; and n is an integer from 0 to four; or a pharmaceutically acceptable salt thereof.

Preferred compounds within the scope of Formula I include those wherein $R_1$ is halogen; n is 1; $R_2$ is lower alkyl; M is hydroxy; and $R_3$ is hydrogen or lower alkyl. More preferred compounds useful in the therapeutic method of this invention include those wherein $R_1$ is 5-fluoro; n is 1; $R_2$ is methyl; M is hydroxy; and $R_3$ is hydrogen.

The most preferred compound of Formula I for treating acne is exisulind. The chemical formula of exisulind is (Z)-5-fluoro-2-methyl-1-[[4-(methylsulfonyl)phenyl] methylene]indene-3-yl acetic acid. The cGMP-specific PDE inhibitory characteristics of exisulind are reported in U.S. Pat. No. 5,858,694. Clinical studies have demonstrated that exisulind is generally well tolerated by patients, has no reported clinically relevant side effects, and can be used safely by humans.

As used herein, the term "acne" includes the various known types of acne and related skin disorders, including acne vulgaris, acne conglobata, acne fulminans, pyoderma facaile, acne keloidalis, chloracne, and steroid acne. The most common form of acne is acne vulgaris, which is characterized by two types of lesions, inflammatory and noninflammatory. Noninflammatory lesions include open comedones (blackheads) and closed comedones (whiteheads) and are characterized by a lymphocytic infiltrate. Inflammatory lesions can be superficial or deep. Superficial inflammatory lesions include papules and pustules, and deep inflammatory lesions consist of cysts and nodules. Inflammatory lesions include those characterized by rupture of the follicular wall and aggregation of neutrophils and mononuclear cells. Acne vulgaris and the other forms of acne which may be treated by administering a therapeutically effective amount of a compound of Formula I are described in more detail in *Principles and Practice of Dermatology*, Chapter 70: Acne and Related Disorders, W. Mitchell Sams, Jr. and Peter J. Lynch eds., 1990, which is incorporated herein by reference.

As used herein, the term "alkyl" refers to straight, branched or cyclic alkyl groups and to substituted aryl alkyl groups. The term "lower alkyl" refers to $C_1$ to $C_8$ alkyl groups.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "lower alkyl carboxylate" refers to a carboxylate group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional crystallization of diastereomeric salts and the like.

Compounds of Formula I also can exist as geometrical isomers (Z and E); the Z isomer is preferred.

As noted above, preferred compounds within the scope of Formula I include those wherein $R_1$ is halogen; n is 1; $R_2$ is lower alkyl; M is hydroxy; and $R_3$ is hydrogen or lower alkyl. More preferred compounds useful in treating acne include those wherein $R_1$ is 5-fluoro; n is 1; $R_2$ is methyl; M is hydroxy; and $R_3$ is hydrogen.

The most preferred compound of Formula I for treating acne is exisulind, (Z)-5-fluoro-2-methyl-1-[[4-(methylsulfonyl)phenyl]methylene]indene-3-yl acetic acid.

The term "cGMP-specific PDE" refers to enzymes such as PDE5 and any of its isoforms that exhibit cGMP-specific hydrolytic enzyme activities and high affinity cGMP binding.

In clinical studies for uses other than acne, it has been demonstrated that exisulind can be safely administered to human patients. Studies with adult patients with intact colons received exisulind at a dosage of 400 mg/day, and patients who had previously undergone a colectomy received exisulind at a dosage of 600 mg/day. In another study with adult patients, the patients received 500 mg/day of exisulind. In a study involving pediatric patients, the dosage of exisulind used ranged from 250 to 350 mg per day.

In these studies, exisulind is generally well tolerated in patients. There have been no clinically relevant side effects reported. The maximum tolerated dose (MTD) was determined to be 600 mg/day in patients with colectomies, and 400 mg/day in the group with intact colons. These elevations were completely reversible on stopping the drug. Additionally, after a patient with elevated liver enzymes stops receiving the drug for approximately one week, the patient can then safely resume treatment at the same or a lower therapeutic dose, i.e. the dosages mentioned above. The elevations seem to be dose related and have been seen mostly at doses above the maximum tolerated dose. There is one group of 18 patients which received exisulind at a daily dose of 600 mg/day for an extended period of time with no such clinically significant side effects. Thirteen of those patients received exisulind for over three years.

Other examples of cGMP-specific PDE inhibitors include MY-5445, dipyridamol.

Additional compounds that may be useful in the practice of this invention include those disclosed in GB 2 063 249 A, GB 2 063 249 A, EP 0 607 439 A1, U.S. Pat. No. 4,101,548, U.S. Pat. No. 4,001,238, U.S. Pat. No. 4,001,237, U.S. Pat. No. 3,920,636, U.S. Pat. No. 4,060,615, WO 97/03985, EP 0 607 439 A1, U.S. Pat. No. 4,101,548, U.S. Pat. No. 4,001,238, U.S. Pat. No. 4,001,237, U.S. Pat. No. 3,920,636, U.S. Pat. No. 4,060,615, WO 97/03985, EP 0 395 328, U.S. Pat. No. 4,209,623, EP 0 395 328, U.S. Pat. No. 4,209,623, U.S. Pat. No. 5,354,571, EP 0 428 268 A2, U.S. Pat. No. 5,354,571, EP 0 428 268 A2, 807,826, U.S. Pat. No. 3,031, 450, U.S. Pat. No. 3,322,755, U.S. Pat. No. 5,401,774, 807,826, U.S. Pat. No. 3,031,450, U.S. Pat. No. 3,322,755, U.S. Pat. No. 5,401,774, U.S. Pat. No. 5,147,875, PCT WO 93/12095, U.S. Pat. No 5,147,875, PCT WO 93/12095, U.S. Pat. No. 4,885,301, WO 93/07149, EP 0 349 239 A2, EP 0

352 960 A2, EP 0 526 004 A1, EP 0 463 756 A1, U.S. Pat. No. 4,885,301, WO 93/07149, EP 0 349 239 A2, EP 0352 960 A2, EP 0 526 004 A1, EP 0 463 756 A1, EP 0 607 439 A1, EP 0 607 439 A1, WO 94/05661, EP 0 351 058, U.S. Pat. No. 4,162,316, EP 0 347 146, U.S. Pat. No. 4,047,404, U.S. Pat. No. 5,614,530, U.S. Pat. No. 5,488,055, WO 97/03985, WO 97/03675, WO 95/19978, U.S. Pat. No. 4,880,810, WO 98/08848, U.S. Pat. No. 5,439,895, U.S. Pat. No. 5,614,627, PCT US94/01728, WO 98/16521, EP 0 722 943 A1, EP 0 722 937 A1, EP 0 722 944 A1, WO 98/17668, WO 97/24334, WO 97/24334, WO 97/24334, WO 97/24334, WO 97/24334, WO 98/06722, PCT/JP97/03592, WO 98/23597, WO 94/29277, WO 98/14448, WO 97/03070, WO 98/38168, WO 96/32379, and PCT/GB98/03712, which are incorporated herein by reference.

Compounds useful in the practice of this invention may be formulated into pharmaceutical compositions together with pharmaceutically acceptable carriers for oral administration in solid or liquid form, or for intravenous, intramuscular, subcutaneous, transdermal, or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for intravenous administration include solutions containing pharmaceutically acceptable salts or sugars. Pharmaceutically acceptable carriers for intramuscular or subcutaneous injection include pharmaceutically acceptable salts, oils or sugars.

When used in its acid form, a compound of Formula I useful in the practice of this invention can be employed in the form of a pharmaceutically acceptable salt of the acid. For example, sodium or potassium salts can be obtained by neutralizing with an equivalent base (alkali) metal hydroxide, mesylate or tosylate. When the active chemical is a base, it can be used as an acceptable formulation by neutralizing it with a suitable acid such as hydrochloric acid. Carriers such as solvents, water, buffers, alkanols, cyclodextrans and aralkanols can be used. Other auxiliary, non-toxic agents may be included, for example, polyethylene glycols, antimicrobial agents and wetting agents.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve activity in accordance with the desired method of administration (ie., oral or intravenous). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

Examples 1–3 illustrate compounds useful in the practice of the claimed invention. Example 4 describes the clinical results with a 16 year-old patient with acne vulgaris who was treated with exisulind.

EXAMPLE 1

α-( 1-p-Methylsulfonylbenzylidene)-2-Methyl-5-Fluoro-3-Indeny-1-Acetic Acid (A) p -Fluoro-α-methylcinnamic acid p-Fluorobenzaldehyde (200 g, 1.61 mole), propionic anhydride (3.5 g, 2.42 mole) and sodium propionate (155 g, 1.61 mole) are mixed in a 1 liter, three-necked flask flushed with nitrogen. The mixture is heated gradually in an oil-bath to 140° C. After 20 hours, the flask is cooled to 100° C. and poured into 8 liters of water. The precipitate is dissolved by adding potassium hydroxide (302 g) in 2 liters of water. The aqueous solution is extracted with ether, and the ether extracts are washed with potassium hydroxide solution. The combined aqueous layers are filtered, acidified with concentrated HCl, and filtered; and the collected solid washed with water, thereby producing p-fluoro-α-methylcinnamic acid which is used as obtained.

(B) p-Fluoro-α-methylhydrocinnamic acid.

To p-fluoro-α-methylcinnamic acid (177.9 g, 0.987 mole) in 3.6 liters ethanol is added 11.0 g of 5% Pd/C and the mixture is reduced at room temperature under a hydrogen pressure of 40 p.s.i.; uptake is 31–32 lbs. (97% of theoretical). After the catalyst is filtered, the filtrate is concentrated in vacuo to give the product p-fluoro-α-methylhydrocinnamic acid that is used without weighing in next step.

(C) 6-Fluoro-2-methylindanone

To polyphosphoric acid (932 g) at 70° C. on the steam bath is added p-fluoro-α-methylhydrocinnamic acid (93.2 g, 0.5 mole) slowly with stirring. The temperature is gradually raised to 95° C., and the mixture is kept at that temperature for 1 hour. The mixture is allowed to cool and added to 2 liters of water. The aqueous layer is extracted with ether, the ether solution washed twice with saturated sodium chloride solution, 5% $Na_2CO_3$ solution, water, and then dried. The ether filtrate is concentrated with 200 g silica-gel, and added to a five pound silica-gel column packed with 5% ether-petroleum ether. The column is eluted with 5–10% ether-petroleum ether and followed by TLC to give 6-fluoro-2-methylindanone.

(D) 5-fluoro-2-methylindenyl-3-acetic acid

A mixture of 6-fluoro-2-methylindanone (18.4 g, 0.112 g, mole), cyanoacetic acid (10.5 g, 0.123 mole), acetic acid (6.6 g), and ammonium acetate (1.7 g) in dry toluene (15.5 ml) is refluxed with stirring for 21 hours, as the liberated water is collected in a Dean Stark trap. The toluene is concentrated, and the residue dissolved in 60 ml of hot ethanol and 14 ml of 2.2N aqueous potassium hydroxide solution. 22 g of 8.5% KOH in 150 ml of water is added, and the mixture refluxed for 13 hours under nitrogen. The ethanol is removed under vacuum, water (500 ml) is added, and the aqueous solution washed well with ether, and then boiled with charcoal. The aqueous filtrate is acidified to pH 2 with 50% hydrochloric acid, cooled, and the precipitate collected. In this way dried 5-fluoro-2-methylindenyl-3-acetic acid (M.P. 164–166° C.) is obtained.

(E) 5-Fluoro-2-methyl-1-(p-methylthiobenzylidene)-3-indenyl acetic acid.

5-fluoro-2-methyl-3-indenyl acetic acid (15 g, 0.072 mole) p-methylthiobenzaldehyde (14.0 g, 0.091 mole) and sodium methoxide (13.0 g, 0.24 mole) are heated in methanol (200 ml) at 60 degree(s) under nitrogen with stirring for 6 hours. After cooling, the reaction mixture is poured into ice-water (750 ml), acidified with 2.5N hydrochloric acid, and the collected solid triturated with a little ether to produce 5-fluoro-2-methyl-1-(p-methylthiobenzylidene)-3-indenyl acetic acid (M.P. 187–188.2° C.). U.V. in methanol λmax. 348 mµ (E % 500), 258 (557), 258 (495), 353 (513), 262.5 (577), 242.5. (511).

(F) 5-Fluoro-2-methyl-1-(p-methylsulfinylbenzylidene)-3-indenyl acetic acid.

To a solution of 5-fluoro-2-methyl-1-(p-methylthiobenzylidene)-3-indenyl acetic acid (3.4 g, 0.01 mole) in a mixture of methanol (250 ml) and acetone (100 ml) is added a solution of sodium periodate (3.8 g, 0.018 mole) in water (50 ml) with stirring. Water (450 ml) is added after 18 hours, and the organic solvents removed under vacuum below 30° C. The precipitated product is filtered, dried and recrystallized from ethyl acetate to give 5-fluoro-2-methyl-1-(rho-methylsulfinylbenzylidene)-3-indenyl acetic acid. Upon repeated recrystallization upon ethylacetate there is obtained cis-5-fluoro-2-methyl-1-(p-methylsulfinylbenzylidene)-3-indenyl acetic acid, M.P. 184–186° C. U.V. in methanol; λmax 328 (E % 377), 286 (432), 257.5 shldr. (413), 227 (548). Further runs reveal the existence of a second polymorph of cis-5-fluoro-2-methyl-1-(p-methylsulfinylbenzylidene)-3-indenyl acetic acid, M.P. 179–181° C.

(G) 5-Fluoro-2-methyl-1-(p-methylsulfonylbenzylidene)-3-indenyl acetic acid

5-Fluoro-2-methyl-1-(p-methylsulfonylbenzylidene)-3-indenyl acetic acid is prepared by adding sodium methoxide (4.4M in MeOH, 68.5 ml, 0.3 mol) dropwise to a stirred, cooled mixture of 5-fluoro-2-methyl-1-(p-methylsulfinylbenzylidene)-3-indenyl acetic acid (100 g, 0.281 mol) in methanol (250 ml) and acetonitrile (500 ml). Sodium bicarbonate (0.56 mol) and hydrogen peroxide (30% in water, 0.56 mol) are added and allowed to react for 18 hours at −10° C. Excess sodium bicarbonate is filtered off, and cooled filtrate (0° C.) neutralized dropwise to pH 7 with 1M hydrochloric acid (350 ml). The resulting product is then filtered and washed with methanol. A thin layer chromatography system to check for purity utilizes chloroform:methyl isobutyl ketone (8:2); the $R_f$ value is 0.21. A tetrahydrofuran/diisopropyl ether combination can be used for product recrystallization. Reaction yield is 89%. ($R_1$=5-fluoro; $R_2$=$CH_3$; $R_3$=hydrogen; $R_4$=COOH; $R_5$=$CH_3SO_2$; n=1).

Formula: $C_{20}H_{17}FO_4S$

Molecular Mass: 372.41 g/mol

Melting point: 204–206° C.

$^1$H-NMR [ppm] (DMSO-$d_6$): 2.16 (s,3,—$CH_3$); 3.30 (s,3,—$SO_2$—$CH_3$); 3.59 (s,2,—$CH_2$—C=O); 6.70–7.17 (m,3,ar.); 7.38 (s,1,=CH—); 7.78–8.04 (AB,4,—Ph—$SO_2$—). HPLC (C-18 Column, 50% acetic acid (2%)/50% acetonitrile, 1.5 ml/min): 3.21 min IR [cm$^{-1}$] (KBr): 1710 C=O; 1310 S=O; 1180 C—F; 1140 S=O.

α-[1-(p-methylsulfonylbenzylidene)-2-methyl-5-fluoro-3-indenyl]-propionic acid is prepared by the similar procedures known in the art.

EXAMPLE 2

α-(1-p-Methylsulfonylbenzylidene)-2-Methyl-5-Fluoro-3-Indeny-1-Acetic Acid Methyl Ester 5-fluoro-2-methyl-1-(p-methylsulfonylbenzylidene)-3-indenyl acetic acid is prepared by the procedure of Example 1, and converted to the methyl ester derivative by the following procedure. Sodium methoxide (4.4M in methanol, 1.36 ml, 0.006 mol) is added to a stirred cooled solution (0° C.) of 5-fluoro-2-methyl-1-(p-methylsulfonylbenzylidene)-3-indenyl acetic acid (1.04 g, 0.0028 mol) in methanol (5 ml) and acetonitrile (10 ml). After 30 minutes, the reaction mixture is dropped into concentrated hydrochloric acid (50 ml) and extracted with methylene chloride (3×25 ml). The organic layer is extracted with saturated sodium bicarbonate (3×25 ml), dried with sodium sulfate, and concentrated in vacuo. The resulting oil is crystallized from tetrahydrofuran/hexane to yield 0.2 g of the desired compound. The melting point is 165–166° C. ($R_1$=5-fluoro; $R_2$=$CH_3$; $R_3$=hydrogen; $R_4$=COO $CH_3$; $R_5$=$CH_3SO_2$; n=1).

Other methyl esters of compounds of Formula I useful in this invention can be prepared in a similar fashion.

EXAMPLE 3

(Z)-5-Fluoro-2-Methyl-1-(4-Methylsulfonylbenzylidene)-1H-3-Indenyl-(2-Hydroxy)Ethane (A) Methyl-5-fluoro-2-methyl-1H-3-indenylacetate Nitrosomethylurea (99.5 mmol) is added in portions to a cold (0° C.) mixture of aqueous 50% KOH (50 ml) and diethylether (150 ml) at 0° C. The yellow ether solution of diazomethane (Note: explosive) is separated, is washed with water, and is added in portions to a solution of 5-fluoro-2-methylindene-3-acetic acid (90 mmol) in dichloromethane (200 ml). When the evolution of $N_2$ ceases, the reaction is complete. After evaporation of the solvents, the residue is recrystallized from hexane to give methyl 5-fluoro-2-methyl-3-indenylacetate (yield 93%; m.p. 53° C.).

(B) 5-Fluoro-2-methyl-1H-3-indenyl-(2-hydroxy)ethane

To a solution of methyl 5-fluoro-2-methyl-3-indenylacetate (24 g) in dry THF (300 ml) lithiumaluminum hydride (6.9 g) is added. The mixture is stirred at room temperature for 1.5 hours. Excess LiAlH$_4$ is destroyed with saturated aqueous NaHSO$_4$ solution. The organic phase is concentrated in vacuo, and the crude product is purified via silica gel column chromatography elution with methylene chloride. The residue is recrystallized from hexane to give 5-fluoro-2-methyl-1H-3-indenyl-(2-hydroxy)ethane (yield 63%; m.p. 65°–66.5° C).

(C) (Z)-5-Fluoro-2-Methyl-1-(4-Methylsulfonylbenzylidene)-1H-3-Indenyl-(2-Hydroxy) Ethane 5-Fluoro-2-methyl-1H-3-indenyl-(2-hydroxy)ethane (15 g, 0.072 mol), p-methylsulfonylbenzaldehyde (14.0 g, 0.091 mol) and sodium methoxide (13.0 g, 0.24 mol) are heated in methanol (200 ml) at 60° C. under nitrogen with stirring for 6 hours. The reaction mixture is poured onto ice-water (750 g), and is acidified with 2.5N hydrochloric acid. The collected solid is triturated with a little ether to produce (Z)-5-fluoro-2-methyl-1-(p-methylsulfonylbenzylidene)-1H-3-indenyl-(2-hydroxy)ethane. Recrystallization of the crude reaction product results in the separation of the mixture of geometrical isomers (Z/E) and gives the title compound ($R_1$=5-fluoro, $R_2$=$CH_3$, $R_3$=H, $R_4$=$CH_2OH$, n=1, $R_5$=$CH_3SO_2$).

Formula: $C_{20}H_{19}FO_3S$

Molecular Mass: 358.43 g/mol

Melting point: 118° C.

$^1$H-NMR [ppm] (DMSO-$d_6$): 2.14 (s,3,—$CH_3$); 2.71 (t, 2,—$CH_2$—); 3.29 (s,3,—$SO_2$—$CH_3$); 3.55 (m,3,—$CH_2$—O); 4.70 (m,1,—OH); 6.68–7.14 (m,3,ar.);7.30 (s,1,=CH); 7.76–8.03 (AB,4,—Ph—$SO_2$—);

IR [cm$^{-1}$] (KBr): 3440 OH; 1300 S=O; 1170 C—F; 1140 S=O

EXAMPLE 4

Clinical Results With a Patient With Acne Vulgaris

A 16 year-old male patient with acne vulgaris was given a pharmaceutical composition containing 125 mg of a cGMP-specific PDE inhibitor, exisulind (the compound of Example 1) twice daily for 8 weeks. At the end of that time, the patient's acne was observed to decrease noticeably in intensity. Since the patient was tolerating that daily dose quite well, his dose of exisulind was increased to 150 mg twice daily, for an additional 8 weeks. By the end this second 8-week period, the patient's acne had disappeared completely, and the patient reported no adverse side effects, clinically significant or not. The patient continued on drug for six months without any significant manifestations of acne during that time.

The pharmaceutical formulation for the 150 mg-containing pharmaceutical composition taken by this patient contained exisulind (150 mg), lactose monohydrate (207 mg), croscarmellose sodium (15 mg), colloidal silicon dioxide (1 mg), magnesium stearate (6.3 mg), and sodium lauryl sulfate (0.7 mg) encapsulated in a #1 gelatin capsule. The exisulind was obtained from Zambon Group, S.p.A., of Milan, Italy. The pharmaceutical formulation for the 125 mg containing composition was formulated with less exisulind, and more excipients to fill the capsule.

Larger adult dosage forms simply contain more active ingredient, and less excipient. Pediatric or adult doses also may be formulated in tablet form of suitable dosages.

EXAMPLE 5 cGMP-PDE Inhibition Activity cGMP-specific phosphodiesterase activity can be determined using methods known in the art, such as a method using radioactive $^3$H cyclic GMP (cGMP)(cyclic 3',5'-guanosine monophosphate) as the substrate for PDE5 enzyme (Thompson, W. J., Teraski, W. L., Epstein, P. M., Strada, S. J., *Advances in Cyclic Nucleotide Research*, 10:69–92, 1979, which is incorporated herein by reference). Using such techniques, the values of cGMP-specific inhibition set forth in Table I were determined for the compounds above:

TABLE I

| Compound | cGMP-PDE % Inhibition at 10 μM |
|---|---|
| Example 1 | 39 |
| Example 2 | 50 |
| Example 3 | 80 |

It will be understood that various changes and modifications may be made in the details of procedure, formulation and use without departing from the spirit of the invention, especially as defined in the following claims.

What is claimed is:

1. A method of treating acne in a patient with acne, comprising administering to the patient a physiologically effective amount of a cGMP-specific PDE inhibitor.

* * * * *